United States Patent [19]

Tung et al.

[11] Patent Number: 4,788,138
[45] Date of Patent: Nov. 29, 1988

[54] METHOD TO ACHIEVE A LINEAR STANDARD CURVE IN A SANDWICH IMMUNOASSAY

[75] Inventors: Ker-Kong Tung, Carlsbad; Linda K. Cragle, San Diego; Frederick W. Rood, Jr., Fallbrook; Shih-Yun Lee, San Marcos, all of Calif.

[73] Assignee: Beckman Instruments, Inc., Fullerton, Calif.

[21] Appl. No.: 44,099

[22] Filed: Apr. 30, 1987

[51] Int. Cl.$^4$ ................. G01N 33/532; G01N 33/546; G01N 33/574; G01N 33/576

[52] U.S. Cl. ........................................ 435/7; 436/513; 436/533; 436/534; 436/801; 436/803; 436/817; 436/820; 436/827

[58] Field of Search .................... 435/7; 436/548, 533, 436/534, 513, 801, 803, 817, 820, 827

[56] References Cited

U.S. PATENT DOCUMENTS

| | | |
|---|---|---|
| 4,016,143 | 4/1977 | Schuurs . |
| 4,376,110 | 3/1983 | David ................................ 436/513 |
| 4,486,530 | 12/1984 | David ............................ 436/519 X |
| 4,595,661 | 6/1986 | Cragle ............................ 436/533 X |
| 4,659,678 | 4/1987 | Forrest ................................ 436/512 |
| 4,690,890 | 9/1987 | Loor ............................ 435/810 X |

OTHER PUBLICATIONS

Sorenson, *Scand. J. Clin. Lab. Invest.*, 42, 577–583, (1982).
Williams et al., *J. Immunological Methods*, 85, 279–294, (1985).
Zvaigzne et al., *Clin. Chem.*, 32(3), 437–440, (1986).
Raab, *Clin. Chem.*, 29 (10), 1757–1761, (1983).
Atkins, *J. Clin. Chem. Clin. Biochem.*, 19, 441–445, (1981).
Marschner et al., *J. Clin. Chem. Clin. Biochem.*, 18, 105–109, (1980).
Hawker et al., *Clin. Chem.*, 27 (1), 14–17, (1981).
Cverna et al., *Clin. Chem.*, 32 (7), 1307–1310, (1986).
Painter et al., *J. Clin. Lab. Automation*, 3 (3), 179–182, (1983).
Dona, *J. Immunological Methods*, 82, 65–75, (1985).

*Primary Examiner*—Sidney Marantz
*Attorney, Agent, or Firm*—William H. May; Arnold Grant; Julia E. Abers

[57] ABSTRACT

A method for obtaining an actual linear standard curve in a sandwich type of immunoassay where a first antibody bound to an insoluble support and a second unbound labelled antibody complex with the antigen contained in a test sample to form an insoluble antibody:antigen:labelled antibody complex which is then detected. Unbound unlabelled first antibody and/or unbound unlabelled second antibody are added to the reaction mixture to divert excess antigen away from the desired end-product complex, thus rendering the antigen of interest the rate-limiting factor in the overall immunoreaction. This results in a pseudo first-order reaction which produces an actual linear standard curve.

27 Claims, 3 Drawing Sheets

METHOD TO ACHIEVE A LINEAR STANDARD CURVE IN A SANDWICH IMMUNOASSAY

FIELD OF THE INVENTION

This invention relates to a method for obtaining a linear standard curve in a sandwich type of immunoassay.

BACKGROUND OF THE INVENTION

This invention, like other immunoassay techniques, is a process for determining the presence of, or the amount of, antigen in a fluid sample, such as a patient's blood or urine. Unlike other immunoassay techniques, the present invention simplifies the immunoassay procedure by providing a method for obtaining a linear standard curve, particularly in the situation where high concentrations of antigen are to be measured.

An antigen is a substance, usually a protein or carbohydrate, that when introduced into the body stimulates the production of an antibody. One example of an antigen is a foreign substance in the body which causes disease, such as a virus.

Another example of an antigen is a substance which evidences a condition of the body. Such antigens are of diagnostic significance. For example, the presence of the antigen IgE (immunoglobulin E) is indicative of an allergy condition, while the antigen hCG (human Chorionic Gonadotropin) is an indication of pregnancy. The antigen ferritin, an iron containing protein, is usually measured as an indication of one of two conditions: (1) anemia (where ferritin is present in relatively low concentrations); and, (2) iron overload (where ferritin is present in relatively high concentrations). These are just a few exemplars of antigens which are of diagnostic use in immunoassays.

Immunoassay techniques rely upon the formation of a complex between the antigen being assayed and an antibody or antibodies. The antibodies are reagents which are added during the immunoassay procedure. Means are provided whereby the amount of complexed antigen and antibody is detectable. Ordinarily, detection is accomplished through the use of a label. The label may, for example, be a radioactive label, such as $I^{125}$, an enzyme label, such as horseradish peroxidase (HRPO), or a fluorescing label, such as fluorescein, although other labelling means are possible. The label is attached to one of the members which form the antigen:antibody complex and is usually detected and/or quantified subsequent to separation of the complexed labelled antigen and antibody from the uncomplexed labelled antigen or antibody.

There are several known methods of immunoassay employing antibodies which are labelled so as to be analytically identifiable. "Sandwich" or "two-site" techniques involve the formation of a complex between the antigen, and two antibodies which bind to two different locations on the surface of the antigen, in such a way that the antigen is said to be "sandwiched" between the two antibodies, as disclosed in U.S. Pat. No. 4,016,143. A convenient method of detecting the amount of antigen:antibody:antigen complex formed in such techniques is to provide a first unlabelled antibody bound to a solid phase support and a second unbound labelled antibody. In this manner, the label becomes bound to the solid support through the antibody:antigen:antibody sandwich, and the labelled complex can readily be isolated. In the standard approach, the amount of label on the solid support is detected and/or quantified, although, in one rarely used variation of the sandwich immunoassay, the amount of label remaining in solution may be measured.

The terms first antibody and second antibody are used herein for the sake of clarity and are not intended to indicate, or limit, the direction of the immunoreaction. For example, the immunoassay can proceed in a forward, fast forward, simultaneous, or reverse mode, as is known in the art. See for example, U.S. Pat. No. 4,376,110. E.g., the antigen can react first with the bound antibody and then with the labelled antibody or vice versa. The reactions can also take place simultaneously. In the case of fast forward and simultaneous assays, only one incubation is used to effect complex formation, while forward and reverse assays require at least two incubations. Pursuant to one or more such incubations, the label becomes attached to the support through the insolubilized antibody:antigen:labelled antibody sandwich. The amount of labelled antibody on the solid support, or the amount remaining in solution, can then be detected.

The sandwich immunoassay has become widely attractive in the clinical and diagnostic testing industry, due to its high degree of specificity. However, with this type of immunoassay, it is often difficult to produce an actual linear standard curve. What is meant by an actual linear standard curve is a standard curve which is relatively linear, i.e., usually about 90-105% linear, as produced within the system itself. This is to be distinguished from a visually linear standard curve, wherein the relative linearity is achieved through mathematical manipulation.

In the particular case of assays where a significant amount of antigen is to be measured, the production of an actual linear standard curve is frequently an impossible task. This is because the antigen, when it is present in significant amount, cannot act as the limiting factor in the reaction system. In contrast, where the antigen of interest is present in sufficiently low quantity, the antigen becomes the rate-limiting factor in the immunoassay, thus naturally creating a pseudo first-order reaction and producing a linear standard curve.

By way of background, chemical reactions can be classified on a kinetic basis, that is, by reaction order, depending on the manner in which the reaction rate is influenced by the concentration of reactants under a given set of conditions. A first-order reaction is one which proceeds at a rate directly proportional to the concentration of one reactant only. The simplest example of a first-order reaction is where the rate of the reaction A→P is exactly proportional to the concentration of A. This is what happens, for example, in the case of isotope decay. An assay based on a first-order reaction will ordinarily produce a linear standard curve.

In a second-order reaction, the reaction rate is proportional to the product of the concentration of two reactants or to the second power of the concentration of a single reactant. An example of the former is the reaction A+B→P. An example of the latter is the reaction 2A→P. An assay based on a second-order reaction, particularly a second-order reaction of the former type, will ordinarily produce a nonlinear standard curve. This is because the reaction rate is dependent on the concentration of more than one reactant. This holds true for third-order reactions, fourth-order reactions, and so forth.

A second-order reaction, such as A+B→P, or, for example, a third-order reaction, such as A+B+C→P, may, under certain circumstances, appear to be a first-order reaction. For example, if the concentration of B and/or C is very high and that of A is very low, the reaction might appear to be first-order, because its rate will be nearly proportional to the concentration of only one reactant, namely, A. In this instance A will act as the rate-limiting factor. Under these particular conditions, the reaction is an apparent or pseudo first-order reaction.

A sandwich immunoassay may generally be regarded as a third-order reaction, represented by the equation:

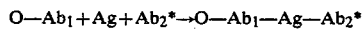

$$O-Ab_1 + Ag + Ab_2^* \rightarrow O-Ab_1-Ag-Ab_2^*$$

wherein $O-Ab_1$ is an insolubilized antibody, Ag is the antigen of interest, and $Ab_2^*$ is the labelled antibody that completes the sandwich. In the case of a sandwich immunoassay where the antigen of interest is in very low concentration, the antigen naturally acts as the rate-limiting factor in the overall reaction. Thus, in this limited application, the immunoreaction becomes a pseudo first-order reaction with the reaction rate being nearly proportional to the concentration of the antigen sought to be measured. This enables the production of a linear standard curve.

In broader applications, where the antigen of interest is not present in sufficiently low quantities to naturally act as the rate-limiting factor in the overall immunoreaction, a nonlinear standard curve will result. It would be desirable to also achieve a linear standard curve in sandwich immunoassays of this type for several reasons. Among other things, a linear standard curve enables one to achieve single point calibration which, in turn, results in decreased cost in running the immunoassay as well as increased convenience for the operator. For purposes of single point calibration, a single standard is run alongside of a blank. The standard will yield the single point, while the blank defines the y-intercept of the standard curve. Because the standard curve is a straight line, only two points are necessary to define the curve. A single conversion factor can be calculated from this curve.

In the case of a nonlinear standard curve, an average of five standards will ordinarily have to be run in order to plot the curve. This becomes quite expensive where a new standard curve is prepared for each batch of immunoassays that are run. Moreover, a linear standard curve will give more accurate results than a nonlinear standard curve. This is because there is a certain amount of error inherent in curve-fitting the nonlinear standard curve.

For these reasons, various attempts have been made to achieve linear standard curves in sandwich immunoassays which are designed to measure an antigen that is not present in sufficiently low quantity to yield a pseudo first-order reaction under typical assay conditions.

One of the most common approaches to this problem has been to adjust the following two parameters present in the sandwich immunoassay system: (1) the amount of insolubilized first antibody; and/or (2) the amount of labelled second antibody. Specifically, the amount of insolubilized first antibody and/or the amount of labelled second antibody in the immunoassay system is increased pursuant to this approach. By increasing the antibody concentration, the antigen becomes the rate-limiting factor in the system, and a pseudo first-order reaction is created. The adjustment of these parameters is, however, limited in its practical application.

The first parameter concerns the addition of excess insolubilized first antibody to the immunoassay system. However, the amount of antibody which can be insolubilized is necessarily limited by the amount of solid support in the system, often the amount of bead surface, and by the coating method used. In other words, there is a finite limit to the amount of antibody which can be effectively bound to the surface of a given solid support.

The second parameter available for adjustment, under prior art methods, is the addition of excess labelled antibody. This parameter, too, is limited in that the labelled antibody which is added to the system inherently increases the background level of the standard sandwich immunoassay. The background of a system is determined by the measurement obtained when a blank, containing only reagent and none of the substance to be measured, is run in the system. In an immunoassay system, the blank contains no antigen, thus precluding the possibility of the formation of the sandwich complex of insolubilized antibody:antigen:labelled antibody in a sandwich immunoassay.

In an ideal sandwich immunoassay system, there should be no labelled antibody attached to the solid phase when a blank is run, due to the absence of any antibody:antigen:antibody sandwich. Thus, theoretically, one should not be able to detect the presence of label on the insolubilized support. Nevertheless, under the imperfect conditions pursuant to which immunoassays are run, a certain amount of the labelled antibody will be nonspecifically adsorbed directly onto the solid support during the immunoassay. This nonspecific adsorption contributes to an elevated blank reading; i.e., detectable label on the insoluble support which is not related to the formation of the sandwich sought to be measured. Where additional labelled antibody is added to the system, there will be additional nonspecific adsorption and, thus, a higher background level. An increased background level adversely affects the sensitivity of an immunoassay. The prior art addition of excess labelled antibody is, therefore, limited by the amount of increased background the immunoassay system is able to tolerate without suffering a loss of sensitivity.

Yet another approach which has been taken deals with mathematical manipulation of the standard curve in order to achieve a visually linear curve. This is in contrast to the first prior art approach described above wherein the level of antibodies in the system is adjusted in an attempt to achieve an actual linear standard curve. A technique known as logit transformation underlies this second approach. Most simply stated, logit transformation results in a semilogarithmic plot of the relationship between absorbance and antigen quantity. In such a plot, the relationship between absorbance and antigen concentration can be approximated by a linear function, in a limited analytical range, as described by Sorenson, *Scand. J. Clin. Lab. Invest.*, 42, 577–589 (1982).

Linearization by logit transformation is more fully described by Williams et al, *J. Immunological Methods*, 85, 179–294 (1985). Generally, these procedures require relatively sophisticated computers to perform a least squares solution to the equation represented by the nonlinear standard curve. While a linear approximation of the transformed curve can be made based on this approach and a conversion factor can be calculated from the data, the necessity of running a full standard curve, rather than a single standard, remains.

More recently, Zvaigzne et al., *Clin. Chem.*, 32 (3), 437–440 (1986), developed a procedure wherein the nonlinear standard curve is stored in a computer. Zvaigzne et al. then run a single standard, on the occasion of subsequent assays, in order to update the y-intercept of the transformed nonlinear standard curve. In this respect, Zvaigzne et al. achieve a form of single point calibration in the context of their method. This approach, however, only operates effectively for extremely stable reagent systems. Moreover, the method requires relatively sophisticated computerized equipment, and it cannot completely alleviate a certain amount of error which is inherent in the curve-fitting process.

Accordingly, there is a need for a method of providing an actual linear standard curve in sandwich immunoassays designed to detect and/or measure antigen present in sufficient quantity such that prior art adjustments to the immunoassay system fail to yield a linear standard curve. It is an object of the present invention to provide such a method. It is a further object of the present invention to provide a method for calibrating a standard curve wherein only a single standard need be run, and which single standard can be used to prepare a conversion factor to the absence of sophisticated and/or expensive computerized equipment.

SUMMARY OF THE INVENTION

According to the present invention, excess first antibody not bound to the solid support and/or excess unlabelled unbound second antibody are added to the immunoassay sytem. Again, the terms first antibody and second antibody are used for the sake of clarity and simplification and are not intended to limit the present invention. The first unbound unlabelled antibody need only act as an analogue for the first antibody bound to the insoluble support. The first unbound unlabelled antibody may, indeed, be a different antibody from the first antibody which is insolubilized. The same holds true for the unbound unlabelled second antibody. I.e., it may be a different antibody from the labelled second antibody for which it acts as an analogue.

The addition of first antibody not bound to the insoluble support is not limited by the surface area available on the insoluble support. The addition of unlabelled unbound second antibody will not increase the background of the immunoassay. The addition of one or both of these analogues will, however, enable one to achieve a pseudo first-order reaction and, thus, a linear standard curve. The advantages of the present invention over prior art methods will become clear after consideration of the accompanying drawings and the following detailed description of the invention.

DETAILED DESCRIPTION OF THE INVENTION

Figure 1:
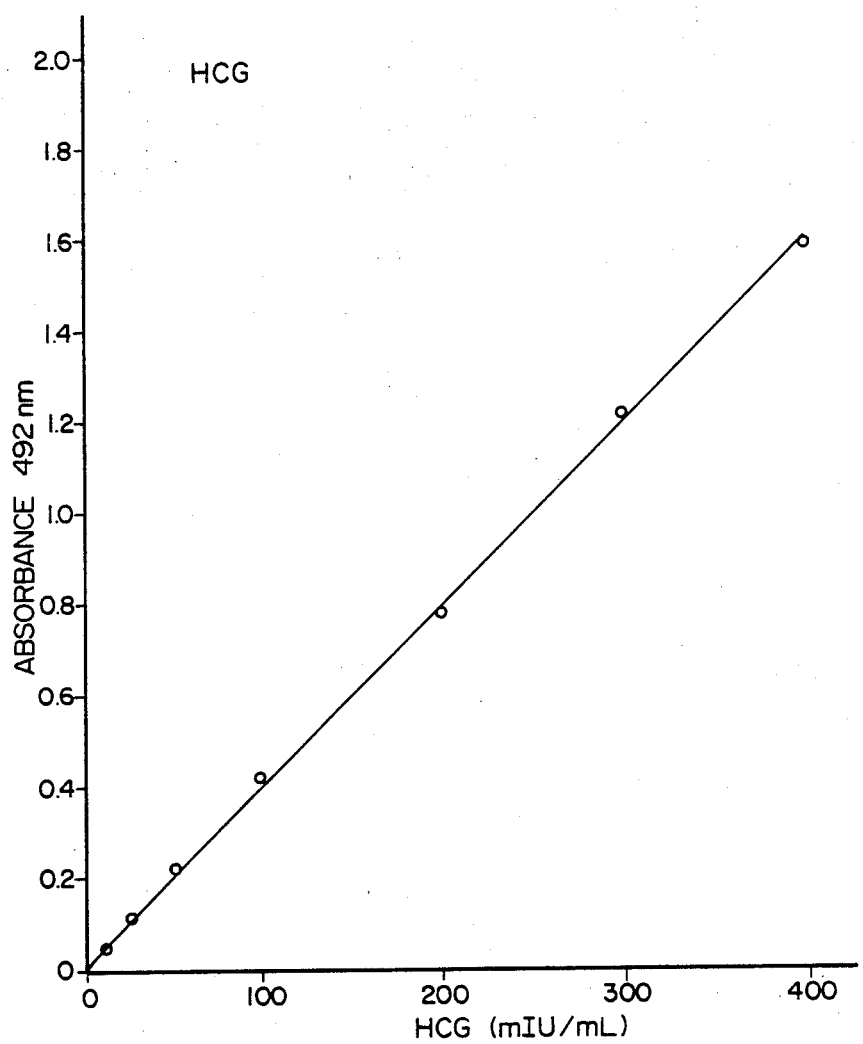
FIG. 1 is a graph illustrating the linear standard curve achieved in an immunoassay for hCG (human Chorionic Gonadotropin), generally present in minute quantities, under typical immunoassay conditions with only prior art adjustments being made to the system.

According to the present invention, excess first antibody not bound to the solid support and/or excess unlabelled unbound second antibody are added to a sandwich immunoassay system. Surprisingly, the addition of either or both of these antibodies was found to increase the parameters available for adjusting the immunoassay system. This enabled an actual linear standard curve to be obtained in immunoassays where the antigen of interest is present in sufficiently high quantities such that an actual linear standard curve is ordinarily unobtainable by prior art methods.

The present invention provides two additional parameters available for adjustment in a sandwich immunoassay in order to obtain a pseudo first-order reaction and, thus, a linear standard curve. Pursuant to the present invention, the two additional parameters take the form of additional reactants, or analogues, which are added to the sandwich immunoassay to divert excess antigen away from the desired end product. This diversion is accomplished through the formation of additional by-products to those ordinarily formed in a sandwich immunoassay.

Prior art sandwich immunoassays ordinarily produce only a small amount of the following by-products to the desired reaction producing the $O-Ab_1-Ag-Ab_2^*$ end product:

| | |
|---|---|
| $O-Ab_1-Ag$ (incomplete sandwich) | I. |
| $Ag-Ab_2^*$ (incomplete sandwich) | II. |

The labelled by-product, $Ag-Ab_2^*$ (II), is soluble and does not contribute to the amount of bound label which is standardly correlated to the amount of antigen present in the sample. In the unusual situation where the amount of unbound label remaining in solution is detected as an indication of the amount of antigen present in a test sample, the labelled by-product (II) will contribute slightly to the signal.

Where only unbound first antibody is added to an immunoassay system, in accordance with the teachings of the present invention, the following by-products are formed in addition to by-products I and II:

| | |
|---|---|
| $Ab_1-Ag-Ab_2^*$ (unbound, labelled sandwich) | III. |
| $Ab_1-Ag$ (incomplete sandwich) | IV. |

Where only unbound unlabelled second antibody is added to an immunoassay system, different by-products are formed in addition to by-products I and II, namely:

| | |
|---|---|
| $O-Ab_1-Ag-Ab_2$ (bound, unlabelled sandwich) | V. |
| $Ag-Ab_2$ (incomplete sandwich) | VI. |

In the case where both unbound first antibody and free, unlabelled second antibody are both added to an immunoassay system, in accordance with the teachings of the present invention, all of by-products I–VI will be formed, as well as the following additional by-product:

| | |
|---|---|
| $Ab_1-Ag-Ab_2$ | VII. |

In the case of by-products III–VII, the only additional labelled by-product, produced pursuant to the present invention, $Ab_1$—Ag—$Ab_2$* (III), is soluble and will not contribute to the amount of signal detected on the soluble support.

By-products have traditionally been considered to be undesirable in an immunoassay. This is because reaction by-products consume small quantities of the antigen of interest, yet do not represent the desired end-product which is sought to be detected and/or quantified. In the case where the amount of label bound to the insoluble support is detected as an indication of the amount of antigen present in the sample being assayed, as is the usual situation, none of the by-product contributes to the signal being measured. The increased formation of reaction by-product has, thus, traditionally been viewed as detracting from the integrity of an immunoassay.

It has, however, unexpectedly been found that the additional by-products, formed pursuant to the present invention, will not adversely affect the accuracy of an immunoassay. This is because the rate of formation of by-products appears to bear a constant relationship to the quantity of antigen present in a test sample. In other words, increased antigen concentration will result in increased by-product formation, and this increase was found to occur in a straight line manner.

It was also found that the unbound first antibody of the present invention acts as an analogue for the first antibody bound to the solid support in a typical sandwich immunoassay. Likewise, the unlabelled second antibody of the present invention acts as an analogue for the labelled second antibody in a sandwich immunoassay. These analogues, individually or together, effectively raise the concentration of first antibody and/or second antibody in the immunoassay system relative to the amount of antigen being assayed, thus creating a pseudo first-order reaction. Based on this principle, actual linear curves have been obtained in immunoassays where, typically, the antigen concentration is sufficiently high such that prior art methods for obtaining an actual linear standard curve have proven to be ineffective or insufficient.

The advantages of the present invention, over prior art methods for obtaining an actual linear curve in a sandwich immunoassay, are seen by reference to the following examples. In the interests of simplicity and clarity, the following examples show only the aspect of the invention which utilizes the addition of unbound first antibody, it being understood that the addition of unlabelled unbound second antibody will operate in a similar manner.

In these examples, simultaneous sandwich immunoassays were run using a first antibody coated onto a polystyrene bead and a second antibody conjugated with horseradish peroxidase (HRPO) which acts as an enzyme label. The polystyrene beads were coated to capacity with the designated first antibody for a particular immunoassay. The amount of labelled second antibody was quantified according to HRPO enzyme activity, with one unit of HRPO activity being roughly equivalent to 1 μg of labelled antibody. Following a first incubation, wherein the antibody:antigen:antibody complex was formed, the insolubilized complex was isolated and subjected to a second incubation wherein a substrate solution for the enzyme label was added in order to produce a detectable signal. The amount of signal bound to the insoluble support was then quantified.

Example 1

Reagents:
(1) Beads: polystyrene bead coated with $Ab_1$
(2) Conjugate solution: buffer, animal protein and $Ab_2$—HRPO
(3) Substrate solution: buffer, $H_2O_2$, and o-phenylenediamine (OPD)

Procedure:
The conjugate solution contains 0.5 U of $Ab_2$—HRPO. The assay is carried out by incubating 20 μl of sample with 250 μl of conjugate solution and an $Ab_1$-coated bead for 20 minutes at room temperature with shaking. After the first incubation, the bead is washed and reincubated with 300 μl of substrate solution for 20 minutes at room temperature. The reaction is then stopped with 1.0 ml of 0.9N sulfuric acid and measured for absorbance at 492 nm on a spectrophotometer. Table I summarizes the results, which are also shown in FIG. 1.

TABLE I

| hCG (mIU/l) | Absorbance at 492 nm |        |       |       |       |       |       |
|---|---|---|---|---|---|---|---|
|             | 10   | 25  | 50  | 100 | 200  | 300  | 400  |
|             | .045 | .11 | .22 | .42 | .778 | 1.25 | 1.59 |

This example illustrates a sandwich immunoassay for hCG (human Chorionic Gonadotropin) under typical assay conditions. The hCG antigen is ordinarily present in relatively minute quantities, thus requiring an assay method of extremely high sensitivity. The measurement range for hCG in a test sample is approximately 1 to 100 mIU/ml, or approximately $2 \times 10^{-12}$M to $2 \times 10^{-10}$M. In the reaction mixture itself, the actual concentration of hCG is less than $10^{-11}$M. This concentration is sufficiently low that the prior art approach of increasing the $Ab_2$* concentration is effective in achieving the conditions for a pseudo first-order kinetic reaction and, thus, a linear standard curve.

Example 2

Reagents:
(1) Beads: polystyrene bead coated with $Ab_1$
(2) Conjugate solution: buffer, animal protein and $Ab_2$—HRPO
(3) Substrate solution: buffer, $H_2O_2$, and o-phenylenediamine (OPD)

Figure 2:
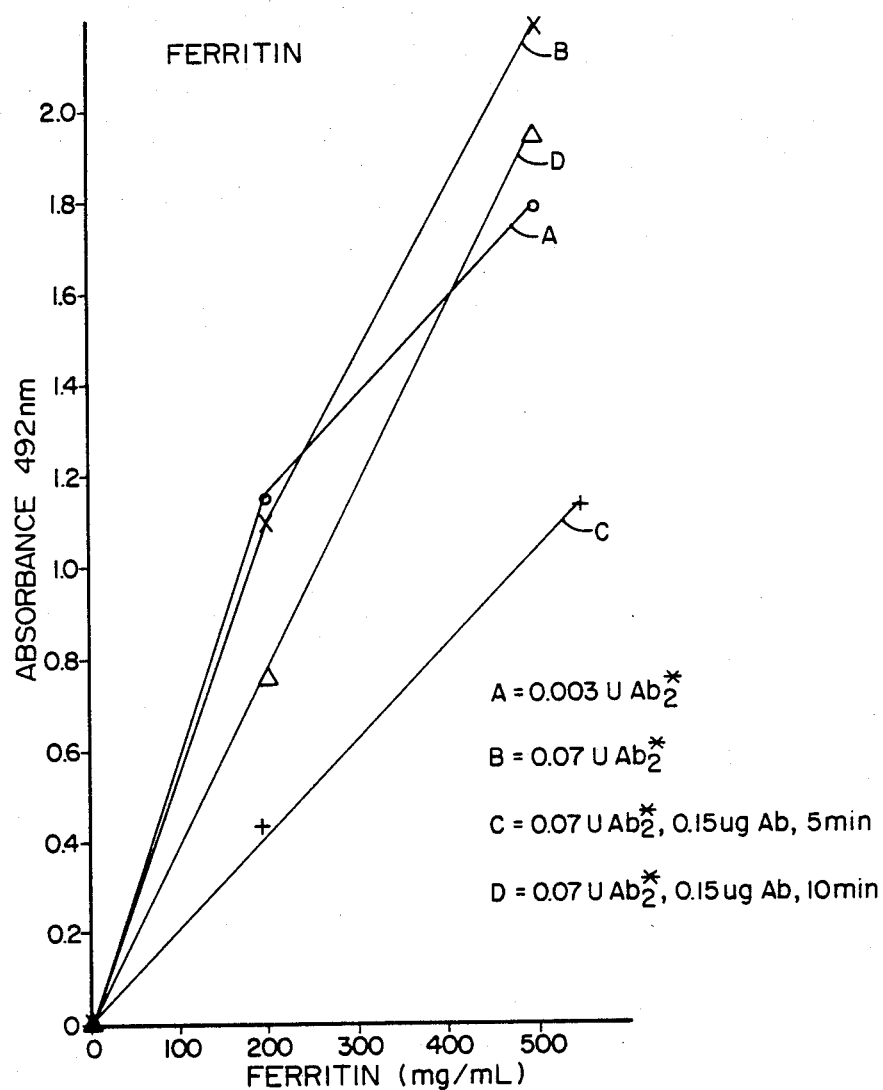
FIG. 2 is a graph illustrating the nonlinear standard curve achieved in an immunoassay for ferritin under typical prior art immunoassay conditions and the linear standard curve achieved pursuant to the teachings of the present invention.

Procedure:
The assays were conducted by incubating 25 μl of sample with 300 μl of conjugate solution and an $Ab_1$-coated bead for 45 minutes at room temperature with shaking, followed by bead washing, and a second incubation with the substrate solution. The reaction was then stopped with the addition of 1.0 μl of 0.9N sulfuric acid, and the absorbance measured at 492 nm on a spectrophotometer. Table II summarizes the results, which are also shown in FIG. 2.

TABLE II

| | Absorbance at 492 nm | | |
|---|---|---|---|
| Conjugate solution | 2nd incubation | 200 ng/ml | 500 ng/ml |
| A. 0.003 U $Ab_2$—HRPO/ml | 15 min | 1.15 | 1.79 |
| B. 0.07 U $Ab_2$—HRPO/ml | 3 min | 1.09 | 2.19 |
| C. 0.07 U $Ab_2$—HRPO with 0.15 μg $Ab_1$/ml | 5 min | 0.43 | 1.13 |
| D. Same as C | 10 min | 0.76 | 1.95 |

This example illustrates a sandwich immunoassay for ferritin run under typical assay conditions (A), utilizing prior art adjustments to the system (B), and, finally, utilizing the teachings of the present invention (C) in order to ultimately obtain an actual linear standard curve. In the case of ferritin, the assay range of 5 to 500 ng/ml of ferritin in an average serum sample corresponds to a concentration range of about $1\times10^{-10}$M to $1\times10^{-9}$M. The final concentration of ferritin in the reaction mixture is approximately $10^{-10}$M. As indicated in FIG. 2, without any adjustments to the system, other than maximum loading of $Ab_1$ onto the polystyrene bead, the standard curve is only 60% linear at the elevated end of the assay range. The addition of a 50 fold excess of $Ab_2^*$ improved the linearity of the standard curve up to only 80%.

Unbound, or soluble, $Ab_1$ was introduced into the reaction mixture to operate as an O—$Ab_1$ analogue. The addition of soluble $Ab_1$ is believed to have created by-products III and IV, identified above, as follows:

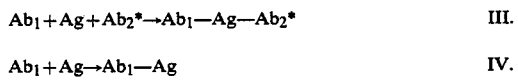

The addition of soluble $Ab_1$ reduced the rate of O—$Ab_1$—Ag—$Ab_2^*$ formation and produced a lower signal as indicated in curve C in FIG. 2. Nevertheless, the presence of $Ab_1$, in addition to $Ab_1$—O, operated to create a pseudo first-order reaction and a linear curve. The signal was improved by increasing the second incubation time to ten minutes (D).

Example 3

Reagents:
(1) Beads: polystyrene bead coated with $Ab_1$
(2) Conjugate solution: buffer, animal protein and $Ab_2$—HRPO
(3) Substrate solution: buffer, $H_2O_2$, and o-phenylenediamine (OPD)

Procedure:
The experiment was carried out by incubating 20 μl of sample with 300 μl of conjugate solution and an $Ab_1$-coated bead at room temperature for 30 minutes with shaking. The bead was then washed, reincubated with 300 μl substrate solution, stopped with 1 ml of 0.9N sulfuric acid and read at 492 nm. Table 3 compares the performance of IgE reagents with and without the combined modifications of the prior art teachings and the teachings of the present invention.

TABLE III

| | Absorbance at 492 nm | | | | |
|---|---|---|---|---|---|
| | IgE (IU/ml) | | | | |
| Conjugate solution | 10 | 25 | 75 | 200 | 400 |
| A. 0.02 U $Ab_2$—HRPO/ml | .15 | .22 | .80 | 1.53 | 1.9 |
| B. 0.1 U $Ab_2$—HRPO and 0.15 μg $Ab_1$/ml | .04 | .105 | .39 | 1.0 | 1.9 |

This example illustrates a sandwich immunoassay for IgE (immunoglobulin E) run under typical assay conditions (A), and also utilizing the combined effect of prior art adjustments to the system and the teachings of the present invention (B) in order to achieve an actual linear standard curve.

Figure 3:
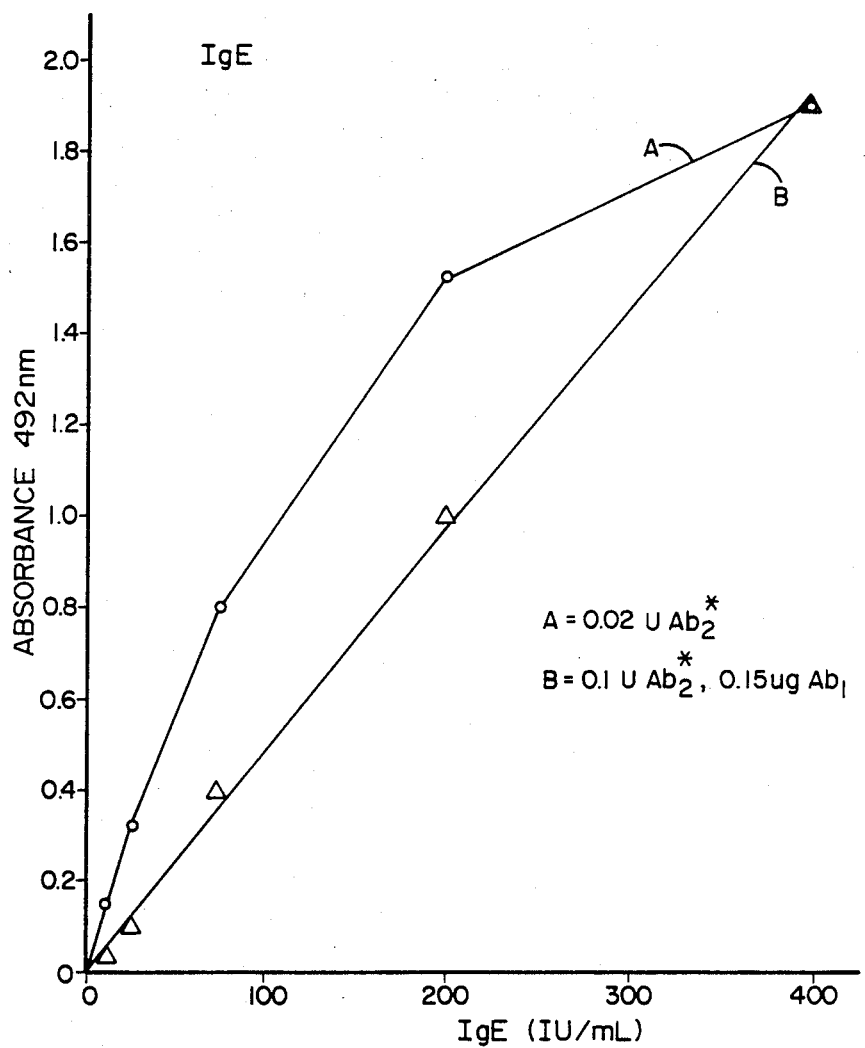
FIG. 3 is a graph illustrating the nonlinear standard curve achieved in an immunoassay for IgE (immunoglobulin E) under typical prior art immunoassay conditions and the linear standard curve achieved pursuant to the teachings of the present invention.

At an assay range of approximately 5 to 400 IU/ml in the test sample, the final concentration of IgE is $10^{-10}$M to $10^{-9}$M in the reaction mixture. Without appropriate adjustment of the parameters of the immunoassay system, the standard curve is less than 50% linear at the elevated end of the assay range. A rather large amount of $Ab_2^*$ and soluble $Ab_1$ was added to produce a linear curve (FIG. 3). This experiment demonstrates that the present invention can handle extreme cases such as IgE without any difficulty.

A comparison of the plots displayed in FIG. 1, FIG. 2, and FIG. 3 demonstrates the effectiveness of the present invention. Unexpectedly, it was found that utilization of the teachings of the present invention enable one to go beyond the prior art limitations, and, thus, obtain an actual linear standard curve in immunoassays where the concentration of the antigen of interest is relatively high.

The antigen hCG, for example, ordinarily present in the reaction mixture at a concentration of less than about $10^{-11}$M, lends itself to effective treatment by prior art methods. Ferritin and IgE, on the other hand, are ordinarily present in the immunoassay reaction mixture at a concentration of approximately $10^{-10}$M, and about $10^{-10}$-$10^{-9}$M, respectively. These concentrations are at least one order of magnitude higher than the hCG reaction mixture concentration and, thus, are ineffectively treated by adjustments to the prior art reaction parameters alone. Through incorporation of the teachings of the present invention, however, actual linear standard curves were achieved for ferritin and IgE immunoassays.

The examples described above are merely examplars of the use of the present invention in ferritin and IgE sandwich immunoassays. It will be apparent to those skilled in the art that variations in the actual processes described in these examples will be useful in other immunoassays. Included in these other immunoassays are assays for the hormones: prolactin, HLH (Human Leutinizing Hormone), FSH (Follicle Stimulating Hormone), Gastrin, PTH (Parathyroid Hormone), HGH (Human Growth Hormone), and ACTH (Adrenocorticotropic Hormone); the infectious disease: hepatitis; the tumor markers: CEA (Carcino-embrionic Antigen), PAP (Prostate Acid phosphatase, and alpha-feto-protein; as well as: CPK—MB (creatine phosphokinase—MB), and insulin, among others. Therefore, the present invention is to be considered limited only by the appended claims.

As used herein, the term "antigen" is intended to include any substance to which antibodies can be produced, and, accordingly, includes within its scope haptens, which may have been rendered antigenic for the purpose of producing antibodies.

As used herein, the term "antibody" is intended to include both polyclonal and monoclonal antibodies, and, further, to include reference to intact antibodies and to fragments thereof which contain the binding region of the antibody. Such fragments may be Fab-type fragments which are defined as fragments devoid of the Fc portion, e.g. Fab, $Fab^1$, and $F(ab^1)_2$ fragments, or may be so-called "half molecule" fragments obtained by reductive cleavage of the disulphide bonds connecting the heavy chain components in the intact antibody.

As this invention may be embodied in several forms without departing from the essential spirit thereof the invention is intended to be defined by the appended claims as opposed to the foregoing description.

What is claimed is:
1. A method for performing an immunoassay for an antigen in a liquid sample comprising the steps of form- ing a complex between the antigen and at least two antibodies, one of said antibodies being a first antibody bound to an insoluble support and one of said antibodies being a second unbound labelled antibody, whereby a portion of said labelled antibody becomes bound to the insoluble support through said complex, and introducing thereto additional antibody selected from the group consisting of unlabelled unbound first antibody, unlabelled unbound second antibody, and mixtures thereof.

2. The method of claim 1 wherein said additional antibody is unlabelled unbound first antibody.

3. The method of claim 1 wherein said additional antibody is unlabelled unbound second antibody.

4. The method of claims 1, 2, or 3 wherein the labelled antibody is labelled with a member selected from the group consisting of radioisotopes, chemiluminescent compounds, bioluminescent compounds, fluorescent compounds, phosphorescent compounds, enzymes, enzyme cofactors, haptens, antibodies, avidin, biotin, carbohydrates, lectins, metal chelators, and derivatives thereof.

5. The method of claim 4 wherein said label is an enzyme.

6. The method of claim 5 wherein said enzyme is horseradish peroxidase.

7. The method of claims 1, 2, or 3 wherein the concentration of antigen in the immunoassay reaction mixture is greater than about $10^{-11}$M.

8. The method of claims 1, 2, or 3 wherein the antigen is selected from the group consisting of prolactin, HLH, FSH, gastrin, PTH, HGH, ACTH, hepatitis, ferritin, CEA, PAP, alpha-fetoprotein, IgE, CPK—MB, and insulin.

9. The method of claim 8 wherein the antigen is selected from the group consisting of ferritin and IgE.

10. A method of achieving a linear standard curve in an immunoassay for the determination of an antigen in a liquid sample comprising the steps of:
   (a) contacting the liquid sample with a first antibody bound to an insoluble support, a second unbound labelled antibody, and additional antibody selected from the group consisting of unlabelled unbound first antibody, unlabelled unbound second antibody, and mixtures thereof, whereby an insoluble complex of bound first antibody:antigen:labelled second antibody is formed, said additional antibody complexing with the antigen to form by-products to the reaction yielding said insoluble complex;
   (b) separating said insoluble complex from the fluid sample, unreacted antibody, and any soluble by-products;
   (c) detecting either the amount of labelled second antibody bound to the insoluble support or the amount of unreacted labelled second antibody.

11. The method of claim 10 wherein said additional antibody is unlabelled unbound first antibody.

12. The method of claim 10 wherein said additional antibody is unlabelled unbound second antibody.

13. The method of claim 10 wherein the amount of labelled antibody bound to the insoluble support is detected.

14. The method of claim 10 wherein the amount of labelled antibody bound to the insoluble support is detected and said additional antibody is unlabelled unbound first antibody.

15. The method of claim 10 wherein the amount of labelled antibody bound to the insoluble support is detected and said additional antibody is unlabelled unbound second antibody.

16. The method of any one of claims 10-15 wherein the labelled antibody is labelled with a member selected from the group consisting of radioisotopes, chemiluminescent compounds, bioluminescent compounds, fluorescent compounds, phosphorescent compounds, enzymes, enzyme cofactors, haptens, antibodies, avidin, biotin, carbohydrates, lectins, metal chelators, and derivatives thereof.

17. The method of claim 16 wherein said label is an enzyme.

18. The method of claim 17 wherein said enzyme is horseradish peroxidase.

19. The method of any one of claims 10-15 wherein the concentration of the antigen in the immunoassay reaction mixture is greater than about $10^{-11}$M.

20. The method of any one of claims 10-15 wherein the antigen is selected from the group consisting of prolactin, HLH, FSH, gastrin, PTH, HGH, ACTH, heptatitis, ferritin, CEA, PAP, alpha-fetoprotein, IgE, CPK—MB, and insulin.

21. The method of claim 20 wherein the antigen is selected from the group consisting of ferritin and IgE.

22. A reagent comprising:
   (a) a first antibody to an antigen, said first antibody being bound to an insoluble support;
   (b) a second antibody to said antigen, said second antibody being unbound and labelled; and,
   (c) additional antibody selected from the group consisting of unlabelled unbound first antibody, unlabelled unbound second antibody, and mixtures thereof.

23. The reagent of claim 22 wherein said additional antibody is unlabelled unbound first antibody.

24. The reagent of claim 22 wherein said additional antibody is unlabelled unbound second antibody.

25. A method of immunoassay for an antigen in a liquid sample comprising the steps of forming a complex between antigen contained in the sample and at least two antibodies, one of said antibodies being a first antibody bound to an insoluble support and one of said antibodies being a second unbound labelled antibody, whereby a portion of said labelled antibody becomes bound to the insoluble support through said complex, and adding thereto an unlabelled unbound analogue for said first antibody.

26. A method of immunoassay for an antigen in a liquid sample comprising the steps of forming a complex between antigen contained in the sample and at least two antibodies, one of said antibodies being a first antibody bound to an insoluble support and one of said antibodies being a second unbound labelled antibody, whereby a portion of said labelled antibody becomes bound to the insoluble support through said complex, and adding thereto an unlabelled unbound analogue for said second antibody.

27. A method of immunoassay for an antigen in a liquid sample comprising the steps of forming a complex between antigen contained in the sample and at least two antibodies, one of said antibodies being a first antibody bound to an insoluble support and one of said antibodies being a second unbound labelled antibody, whereby a portion of said labelled antibody becomes bound to the insoluble support through said complex, and adding thereto unlabelled unbound analogues for said first and second antibodies.

* * * * *